(12) United States Patent
Verschut et al.

(10) Patent No.: US 10,981,527 B2
(45) Date of Patent: Apr. 20, 2021

(54) IMPACT MOTION TRACKING SYSTEM

(71) Applicant: Kistler Holding AG, Winterthur (CH)

(72) Inventors: Roderick Verschut, Speyer (DE);
Thomas Warkentin, Heiligkreuzsteinach (DE); David Stein, Sterling Heights, MI (US)

(73) Assignee: Kistler Holding AG, Winterthur (CH)

( * ) Notice: Subject to any disclaimer, the term of this patent is extended or adjusted under 35 U.S.C. 154(b) by 75 days.

(21) Appl. No.: 16/439,931

(22) Filed: Jun. 13, 2019

(65) Prior Publication Data
US 2019/0381963 A1    Dec. 19, 2019

Related U.S. Application Data

(60) Provisional application No. 62/684,309, filed on Jun. 13, 2018.

(51) Int. Cl.
*B60R 21/0132* (2006.01)
*G01D 5/16* (2006.01)
(Continued)

(52) U.S. Cl.
CPC .......... *B60R 21/0132* (2013.01); *G01D 5/16* (2013.01); *G01P 15/18* (2013.01); *B60R 2021/01315* (2013.01); *G09B 23/30* (2013.01)

(58) Field of Classification Search
CPC .......... G01D 5/16; G01P 15/18; G01C 21/16; G01C 21/165; G01C 21/18; G01M 7/08
See application file for complete search history.

(56) References Cited

U.S. PATENT DOCUMENTS 5,744,953 A    4/1998  Hansen
7,640,106 B1  12/2009  Stokar et al.
(Continued)

FOREIGN PATENT DOCUMENTS

JP     A2015184214    10/2015
WO  WO 2007/058526     5/2007

OTHER PUBLICATIONS

European Search Report, EP Application No. 18179852.1-1222, dated Dec. 21, 2018, 10 pages.
(Continued)

*Primary Examiner* — Dominic E Hawkins
(74) *Attorney, Agent, or Firm* — Dority & Manning, P.A.

(57) ABSTRACT

An impact motion tracking system for tracking an object in a three-dimensional space includes a motion tracking sensor that includes a housing, a magnetic measurement module, an inertial measurement module, and a transmitter module, which generates magnetic fields. The magnetic measurement module measures magnetic fields generated by the transmitter module and has a fixed orientation with the object. The inertial measurement module measures a linear acceleration or an angular acceleration and has a fixed positional relationship with the object. An electronic processor receives measured signals from the motion tracking sensor and derives an impact motion information for the object based on received measured signals from the inertial measurement module. The electronic processor derives a magnetic motion information for the object based on received measured signals from the magnetic measurement module and periodically calibrates impact motion information with magnetic motion information.

17 Claims, 4 Drawing Sheets

(51) Int. Cl.
    *G01P 15/18*    (2013.01)
    *B60R 21/013*   (2006.01)
    *G09B 23/30*    (2006.01)

(56) References Cited

U.S. PATENT DOCUMENTS

| | | | | |
|---|---|---|---|---|
| 8,914,196 | B1* | 12/2014 | Breed | B60R 21/0132 |
| | | | | 701/45 |
| 9,870,722 | B2* | 1/2018 | Fritz | G01M 17/007 |
| 10,059,347 | B2* | 8/2018 | Thieberger-Navon | |
| | | | | B60W 50/0097 |
| 2007/0295089 | A1* | 12/2007 | Velinsky | G01C 17/30 |
| | | | | 73/514.01 |
| 2008/0157940 | A1* | 7/2008 | Breed | B60N 2/853 |
| | | | | 340/425.5 |
| 2009/0278791 | A1* | 11/2009 | Slycke | A61B 5/1114 |
| | | | | 345/156 |
| 2013/0035827 | A1* | 2/2013 | Breed | G01G 19/024 |
| | | | | 701/45 |
| 2014/0357215 | A1* | 12/2014 | Michaelis | H04W 4/027 |
| | | | | 455/404.2 |

OTHER PUBLICATIONS

Fan, Bingfei, et al., "An Adaptive Orientation Estimation Method for Magnetic and Inertial Sensors in the Presence of Magnetic Disturbances," Sensors, vol. 17 No. 5, May 19, 2017, 19 pages.
Japanese Office Action dated Oct. 27, 2020 and Translation, 6 pages.

* cited by examiner

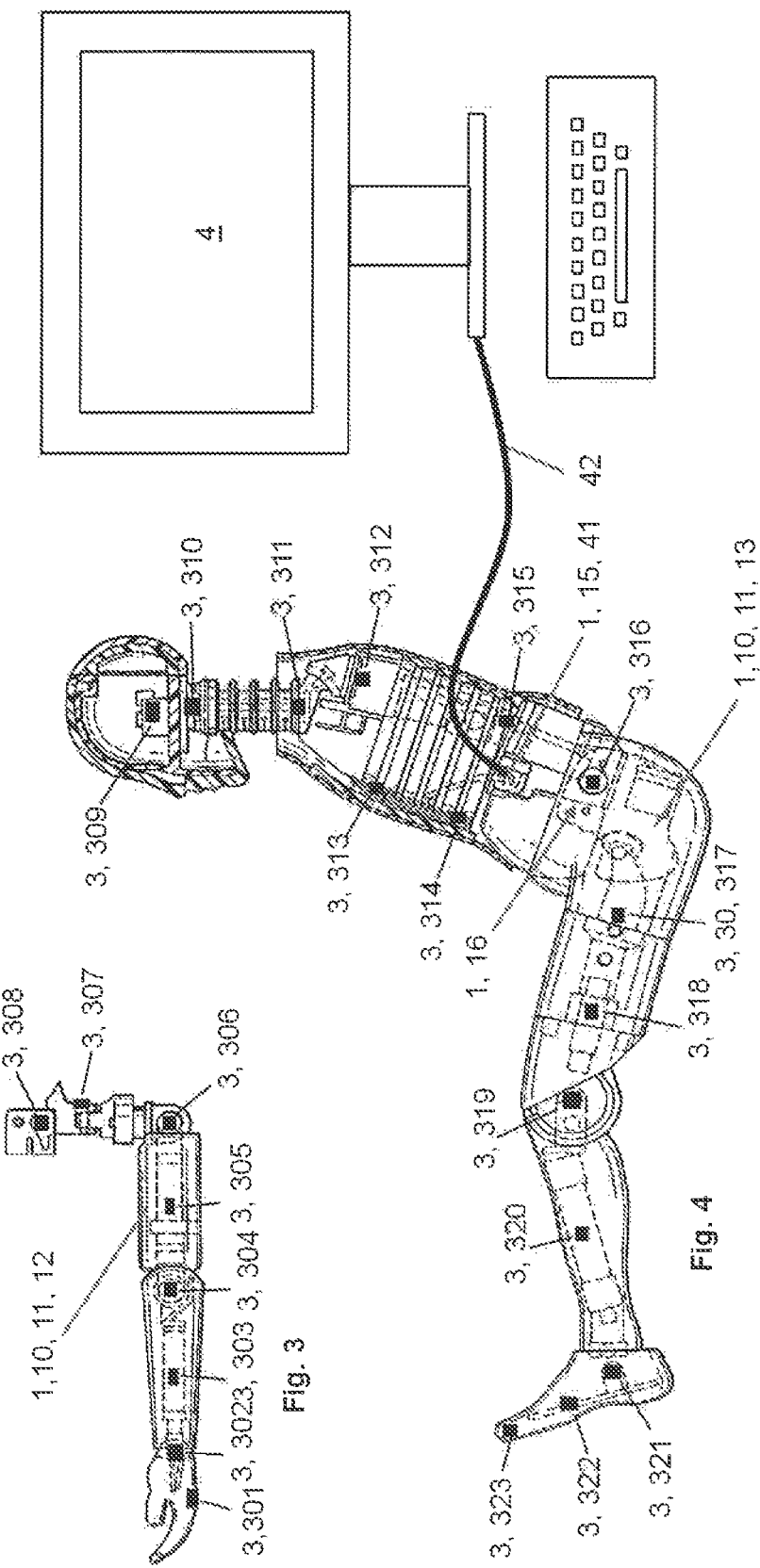

IMPACT MOTION TRACKING SYSTEM

FIELD

The invention relates to an impact motion tracking system for tracking an object in a three-dimensional space.

BACKGROUND

In crash tests as conducted by automotive, aviation, and other vehicle manufacturers, the effect of an impact upon a vehicle and its occupants is determined. In such crash tests, the vehicle undergoes a simulated collision. Both, the vehicle and its occupants, also called crash test dummies, are exposed to high inertial loading in a short period of about 200 msec. As a result, the crashed vehicle and the crash test dummies are subject to a brisk acceleration and a partial deformation. The crashed vehicle and the crash test dummies undergo impact motion like a sled motion of the crashed vehicle or a back and forth head shaking of the crash test dummies. According to the Euro New Car Assessment Program (Euro NCAP) or the US New Car Assessment Program (US NCAP), a limit value for a linear chest acceleration of a crash test dummy is 60 g for a period of time of at least 3 msec, and an angular chest acceleration of a crash test dummy may reach up to 1500°/sec. Thus, impact motion in the sense of present invention means a motion of the crashed vehicle and the crash test dummies induced by a linear acceleration of up to 60 g for a period of at least 3 msec or by an angular acceleration of up to 1500°/sec.

Three-dimensional tracking of the impact motion of the crashed vehicle and of the crash test dummies during and after the simulated collision is performed with a wide variety of high resolution tracking sensors like high speed video cameras, force sensors, acceleration sensors, angle rate sensors, and the like. High resolution tracking in the sense of present invention means tracking of an object in a three-dimensional space with a spatial resolution of less than 2 mm in each of the three dimensions and a time resolution of less than 0.02 msec.

Unfortunately, the impact motion of the interior of the crashed vehicle and of the crash test dummies sitting inside the crashed vehicle cannot always be discerned with satisfactory spatial and time resolution from outside the crashed vehicle by means of high speed cameras, for example due to the existence of non-transparent vehicle surroundings and of the inflation of multiple airbags during the simulated collision.

A solution to this unsatisfactory three-dimensional impact motion tracking might come from sensor fusion. In this regard, WO2007058526A1 describes a motion tracking system for tracking an object in a three-dimensional space comprising a motion tracking sensor and an electronic processor. The motion tracking sensor in turn comprises a sensor fusion of a magnetic measurement module and an inertial measurement module. The magnetic measurement module measures magnetic fields generated by a transmitter module. The magnetic measurement module has a fixed positional relationship with an object portion of the object. The magnetic measurement module comprises three magnetic field sensors placed in a three-dimensional positional relationship with respect to one another. The inertial measurement module measures a linear acceleration and an angular acceleration. The inertial measuring module has a fixed positional relationship with an object portion of the object. The inertial measurement module comprises three linear acceleration sensors and three angular acceleration sensors. The linear acceleration sensors and the angular acceleration sensors are placed in a three-dimensional positional relationship with respect to one another. The electronic processor receives measured signals from the motion tracking sensor. The electronic processor derives a motion information for the object portion of the object based on the received measured signals. This is done by double integration in time of linear acceleration sensor signals and of angular acceleration sensor signals. Gravitation acceleration of the motion tracking system gets subtracted. The electronic processor also periodically calibrates motion information from the inertial measurement module with motion information from the magnetic measurement module. Thus, at regular intervals, motion information from the inertial measurement module is corrected by motion information from the magnetic measurement module.

Such a motion tracking system is commercially available as MTi 100-series products by Xsens Technologies B.V. Unfortunately, the MTI 100 series products do neither possess the structural robustness that is required for crash tests, nor are they apt to measure the magnitude of the linear acceleration and of the angular acceleration as well as the time resolution of the impact motion. The MTi 100 series products measure the linear acceleration with a standard full range of only around 5 g and the angular acceleration with a standard full range of only 450°/sec. Such a restriction is well below the aforementioned impact motion tracking requirements. More importantly, the NTi 100 series products measure only with a sampling rate of 60 kS/sec and an output frequency of up to 2 kHz, which is below the aforementioned high resolution tracking requirement. In other words, the MTI series And the bias repeatability per year is typically 0.03 m/sec$^2$, resulting in an position error of 6 mm after 200 msec, which is far above the required spatial resolution of less than 2 mm in a dimension. Due to these restrictions, the NTi 100 series products are not suited for crash tests.

The aforementioned motion tracking system yields satisfactory results in the absence of ferromagnetic metals which generate distorting magnetic fields. The presence of ferromagnetic metals, however, is commonplace in a great number of devices, including electric wiring, electronic devices, monitors, fluorescent lighting and also automotive vehicles, aviation vehicles and also crash test dummies. Distorting magnetic fields that are superimposed to the magnetic fields generated by the transmitter module falsify the signals measured by the magnetic measurement module and lead to positional inaccuracies of the motion tracking system.

The motion tracking sensor itself is low weight and is easily attached to a moving body by means of a strap or a band, so that it can be worn in a fixed positional relationship with an ankle or a wrist of a human body. During a crash test, however, the acceleration of a crash test dummy is so brisk and the crash test dummy is in so hefty frictional contact with the interior of the crashed vehicle, that a motion tracking sensor attached by means of a strap or a band on a body portion of the crash test dummy cannot maintain a fixed positional relationship with the object portion of the crash test dummy. The loose of the fixed relationship of the motion tracking sensor with the object portion adversely affects the spatial resolution the motion tracking system.

BRIEF SUMMARY

The aim of the invention is to provide an improved impact motion tracking system for crash tests.

This aim is achieved by means of an impact motion tracking system for tracking an object in a three-dimensional space, whereby a motion tracking sensor comprises a housing, a magnetic measurement module and an inertial measurement module; a transmitter module generates magnetic fields; said magnetic measurement module measures magnetic fields generated by said transmitter module, said magnetic measurement module has a fixed positional relationship with at least one object portion of said object; said inertial measurement module measures at least one of a linear acceleration and an angular acceleration, said inertial measurement module has a fixed positional relationship with said at least one object portion; an electronic processor receives measured signals from said motion tracking sensor; said electronic processor derives an impact motion information for said object portion based on received measured signals from said inertial measurement modules; said electronic processor derives a magnetic motion information for said object portion based on received measured signals from said magnetic measurement modules; and said electronic processor periodically calibrates impact motion information with magnetic motion information. Whereby said object is at least one of a crash test dummy and a vehicle to be crashed.

Surprisingly, it has been found out that for a crash test dummy or a vehicle to be crashed, which both contain a certain amount of ferromagnetic metals, the resulting distortion of the magnetic fields generated by said transmitter module can be corrected by knowing the strength of the magnetic field distortion at a reference magnetic measurement module. For said crash test dummy, a magnetic measurement module preferably positioned at a pelvis serves as a reference for other magnetic measurement modules positioned at the back of hand, at the wrist, and the like. And for said vehicle to be crashed, a magnetic measurement module preferably positioned at a trunk serves as a reference for other magnetic measurement modules positioned at a left front bumper, a right front bumper, and the like. During the crash test, said reference magnetic measurement module will not change its position, and also the strength of the magnetic field distortion at said reference magnetic measurement module will not change. In other words, each of said two reference magnetic measurement modules independently establish a center of a three-dimensional coordinate system for independently tracking the impact motion of the crash test dummy and for tracking the impact motion of the vehicle to be crashed. Thus for the impact motion of an object to be tracked, said electronic processor periodically calibrates magnetic motion information from other magnetic measurement modules with referential magnetic motion information from said reference magnetic measurement module. Said calibration of magnetic motion information from other magnetic measurement modules 32 with referential magnetic motion information from a reference magnetic measurement module 32' occurs periodically in time intervals of less than 0.02 msec.

The sensor hardware of said motion tracking sensor has been redesigned to fulfill the aforementioned impact motion tracking requirements. Preferably, said motion tracking sensor withstands an impact motion induced by a linear acceleration of up to 60 g for a period of at least 3 msec or by an angular acceleration of up to 1500°/sec. And also the hardware of said motion tracking system has been redesigned to fulfill the aforementioned high resolution tracking requirement. Preferably, said impact motion tracking system tracks said at least one of a crash test dummy and a vehicle to be crashed with a spatial resolution of less than 2 mm in each of the three dimensions and a time resolution of less than 0.02 msec.

Preferably, said motion tracking sensor has a fixed connection with an object portion of said object, such that during and after the impact motion, a mutual distance between said motion tracking sensor and said object portion to which said motion tracking sensor has a fixed positional relationship changes less than 1 mm. Preferably, said fixed connection is directly made between said housing of said motion tracking sensor and a skeleton of said crash test dummy. Preferably, said fixed connection is directly made between said housing of said motion tracking sensor and an object portion of said vehicle to be crashed.

BRIEF DESCRIPTION OF THE DRAWINGS

The present invention will be described with the aid of exemplary embodiments in connection with the drawings here:

FIG. 3 shows a schematic view of an arm portion of a crash test dummy for the impact motion tracking system of FIG. 1;

FIG. 4 shows a schematic view of a body portion of a crash test dummy for the impact motion tracking system of FIG. 1;

Figure 1:
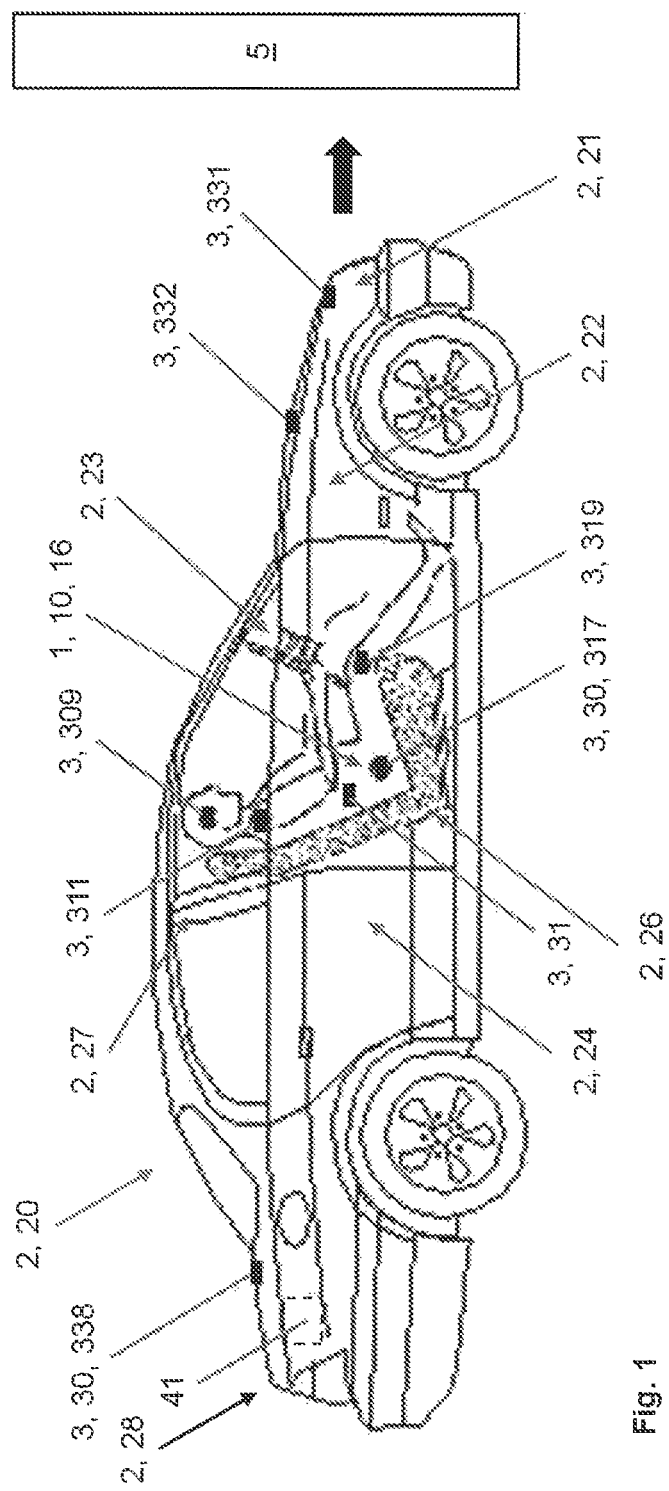
FIG. 1 shows a schematic side view of an impact motion tracking system for tracking at least one of a crash test dummy and a vehicle to be crashed.

DESCRIPTION OF EXEMPLARY
EMBODIMENTS OF THE INVENTION

Reference will now be made in detail to present exemplary embodiments of the invention, wherein one or more examples of which are illustrated in the accompanying drawings. The detailed description uses numerical and letter designations to refer to features in the drawings. Like or similar designations in the drawings and description have been used to refer to like or similar parts of the embodiments of the invention.

Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

It is to be understood that the ranges and limits mentioned herein include all sub-ranges located within the prescribed limits, inclusive of the limits themselves unless otherwise stated. For instance, a range from 100 to 200 also includes all possible sub-ranges, examples of which are from 100 to 150, 170 to 190, 153 to 162, 145.3 to 149.6, and 187 to 200. Further, a limit of up to 7 also includes a limit of up to 5, up to 3, and up to 4.5, as well as all sub-ranges within the limit, such as from about 0 to 5, which includes 0 and includes 5 and from 5.2 to 7, which includes 5.2 and includes 7. Moreover, while specific spatial dimensions are provided for some of the exemplary embodiments described herein, the present invention is not limited to embodiments with those specific spatial dimensions.

FIGS. 1 to 6 show several exemplary embodiments of an impact motion tracking system for an object in a three-dimensional space. The object is at least one of a crash test dummy 1 and a vehicle to be crashed 2. In a crash test, a vehicle to be crashed 2 collides in a simulated collision with an obstacle with a specific velocity. The collision may be a frontal collision, a side collision, a rear collision, a rollover collision, etc. At least one crash test dummy 1 is placed in the vehicle to be crashed 2. A crash test is performed over a relatively short period of time of about 200 msec. During the simulated collision, the crash test dummy 1 is temporarily subjected to a brisk acceleration and the body of the crash test dummy 1 is deformed. Regionally, the crash test is regulated by the Euro New Car Assessment Program (Euro NCAP) or the US New Car Assessment Program (US NCAP), for example. According to these regulations, the body acceleration of the crash test dummy 1 has to comply with certain limit values. Thus, according to Euro NCAP or US NCAP the limit value for the linear chest acceleration of a crash test dummy 1 is 60 g for a period of time of at least 3 msec, where the Earth's gravity is by definition g=9.81 m/sec$^2$. And an angular chest acceleration of the crash test dummy 1 may reach up to 1500°/sec.

FIGS. 1 to 4 show exemplary embodiments of object portions 10 of the crash test dummy 1. The crash test dummy 1 has a high biofidelity, which means that it closely imitates the size, shape, mass, stiffness and energy absorption of an actual human being. The crash test dummy 1 has object portions 10 such as a skeleton 11, an arm portion 12, a body portion 13, a pelvis 16, and the like. Thus, the crash test dummy 1 has a skeleton 11 made from mechanically resistant material such as aluminum, steel, and the like. The crash test dummy 1 also has a skin made from synthetic material such as vinyl polymers, and the like, which skin stretches over the skeleton 11.

Figure 5:
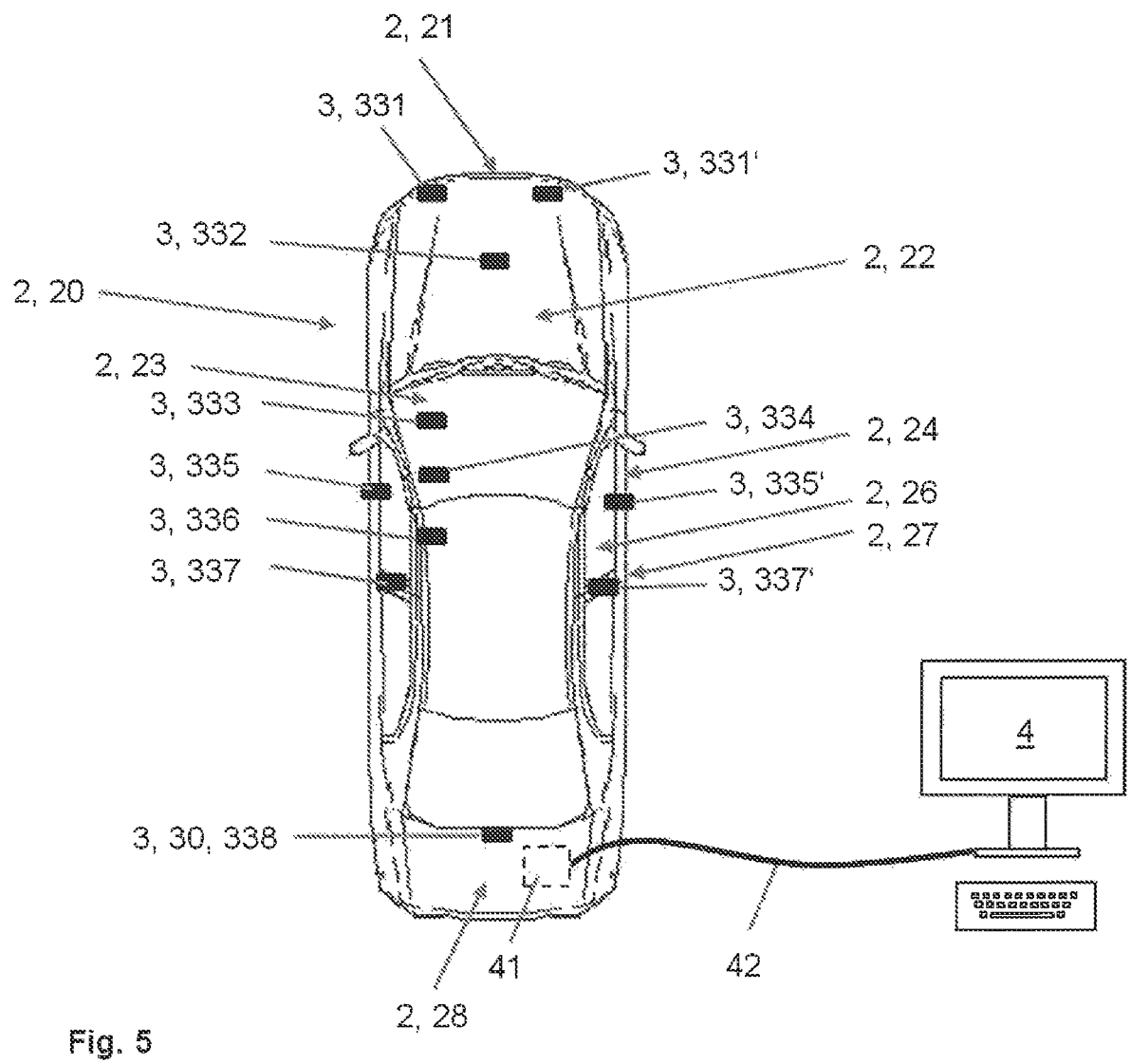
FIG. 5 shows a schematic view of a vehicle to be crashed for the impact motion tracking system of FIG. 1.

FIGS. 1 and 5 show exemplary embodiments of object portions 20 of the vehicle to be crashed 2. The vehicle to be crashed 2 is a self-propelled vehicle from industrial production. The vehicle to be crashed 2 may be a car, a bus, a truck, a train, an airplane, and the like. The vehicle to be crashed 2 has object portions 20 such as a front bumper 21, an engine 22, a steering wheel 23, doors 24, seats 26, a B pillar 27, a trunk 28, and the like.

Figure 2:
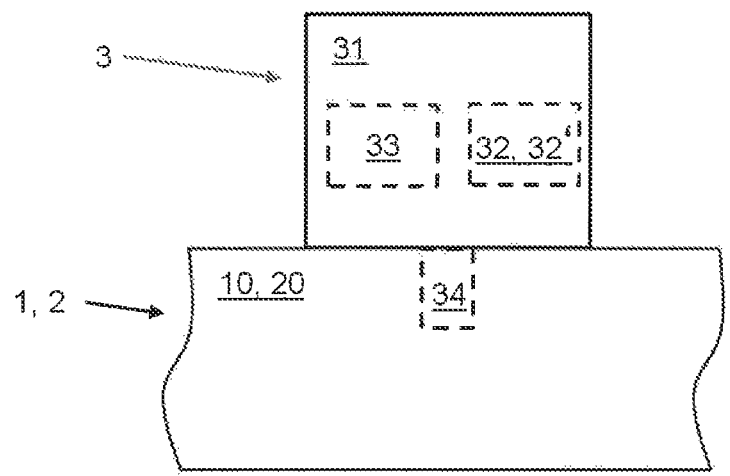
FIG. 2 shows a schematic view of a motion tracking sensor of the impact motion tracking system of FIG. 1.

The impact motion tracking system comprises a motion tracking sensors 3 that are configured to be carried by an object, which desirably can be at least one of a crash test dummy 1 and a vehicle to be crashed 2. FIG. 2 schematically shows an exemplary embodiment of such a motion tracking sensor 3. The motion tracking sensor 3 comprises a housing 31, which contains a magnetic measurement module 32, 32' and an inertial measurement module 33. The housing 31 may be constructed from mechanically resistant material such as aluminum, polypropylene, polycarbonate, and the like. Each of the magnetic measurement module 32, 32' and the inertial measurement module 33 of the motion tracking sensor 3 may be implemented in a micro electro-mechanical system (MEMS). MEMS have small dimensions which generally range from 20 μm to 1 mm.

The impact motion tracking system comprises at least one transmitter module 30 that is configured to be carried by the object. The transmitter module 30 is able to generate magnetic fields that are strong enough to be measured by all of the magnetic measurement modules 32, 32' carried by the object 1, 2. Preferably, for an object in the form of a crash test dummy 1, the transmitter module 30 is placed at the pelvis 16. Preferably, for an object in the form of a vehicle to be crashed 2, the transmitter module 30 is placed at least at one of the engine 22, a seat 26 and the trunk 28. The transmitter module 30 is configured with a range of operation of at least one meter. The transmitter module 30 is configured to generate magnetic fields that are at least as strong as the geomagnetic field with a magnitude of around 50 μT. The transmitter module 30 is configured to generate magnetic fields that are changing with frequencies of at least 100 Hz and up to 2 kHz.

Each magnetic measurement module 32, 32' comprises three mutually orthogonally placed magnetic field sensors that are placed in three-dimensional positional relationship with respect to each other. By means of these three magnetic field sensors, transmitted magnetic fields are independently measured in three dimensions with a time resolution of less than 0.02 msec. For measured magnetic fields, the magnetic measurement module 32, 32' issues magnetic measuring signals. There are many magnetic measuring methods known to those skilled in the art like anisotropic magneto-resistive (AMR) sensors, Lorentz-force-based magnetic field sensors, and the like. Each of the magnetic field sensors of the magnetic measurement module 32, 32' is configured to measure magnetic fields with a standard full range of around 50 μT, a noise of at least 0.5 μT/√Hz and an angular accuracy of at least 1°. The magnetic measurement module 32, 32' is configured to issue magnetic measuring signals with an output data rate of at least 100 Hz and up to 2 kHz.

Each inertial measurement module 33 comprises three linear acceleration sensors and three angular acceleration sensors, the latter are also called gyroscopes. The three linear acceleration sensors and the three angular acceleration sensors are mutually orthogonally placed in a three-dimensional positional relationship with respect to one another. The linear acceleration sensors are configured to measure the linear acceleration as vector lengths in three dimensions. The angular acceleration sensors are configured to measure the angular acceleration as vector angles in three dimensions. Each of the linear acceleration sensors and the angular acceleration sensors is configured to measure the respective linear acceleration and the angular acceleration in three dimensions with a time resolution of less than 0.02 msec. For a measured motion of the object, the inertial measurement module 33 is configured to issue linear acceleration sensor signals and angular acceleration sensor signals. Micromachined inertial measurement modules 33 are known to those skilled in the art like a cantilever beam with a seismic mass, where under the influence of an acceleration the seismic mass gets deflected, which deflection is measured by means of piezoelectric, piezoresistive or capacitive means. In order to fulfill the impact motion requirements for crash tests, a low-weight and high-stiffness inertial measurement module 33 has been developed. Thus, the inertial measurement module 33 is configured to measure the linear acceleration with a standard full range of up to 60 g and a noise of less than 100 μg/√Hz. The inertial measurement module 33 is configured to measure the angular acceleration with a standard full range of up to 1500°/sec and a noise of less than 0.01°/sec/√Hz. The inertial measurement module 33 is configured to issue linear acceleration signals and angular acceleration signals with an output data rate of at least 100 Hz and up to 2 kHz.

The motion tracking sensor 3 is desirably carried by an object by being embedded inside at least one of a crash test dummy 1 and a vehicle to be crashed 2. The motion tracking sensor 3 embedded inside at least one of a crash test dummy 1 and a vehicle to be crashed 2 desirably is provided with electromagnetically shielding materials that shield the motion tracking sensor 3 from distorting magnetic fields. The effectiveness of the shielding depends very much upon the nature and thickness of the shielding materials included with the embedding materials of the at least one of a crash test dummy 1 and a vehicle to be crashed 2.

As shown schematically in FIG. 2, the motion tracking sensor 3 has a fixed connection 34 with an object portion 10, 20 of at least one of the crash test dummy 1 and the vehicle to be crashed 2. During and after the impact motion, a mutual distance between the motion tracking sensor 3 and the object portion 10, 20 of the at least one of a crash test dummy 1 and vehicle to be crashed 2 to which object portion 10, 20 the motion tracking sensor 3 has a fixed positional relationship, changes less than 1 mm. The fixed connection 34 is configured to withstand an impact motion induced by a linear acceleration of up to 60 g for a period of at least 3 msec or by an angular acceleration of up to 1500°/sec. Preferably, the fixed connection 34 is directly made between the housing 31 of the motion tracking sensor 3 and the skeleton 11 of the crash test dummy 1. Preferably, the fixed connection 34 is directly made between the housing 31 of the motion tracking sensor 3 and an object portion 20 of the vehicle to be crashed 2. The fixed connection 34 may be a form closure, a force closure or a material bond. A form closure is a snap fit, a clamp fit, cold rivet, and the like. A force closure is a bolted joint, hot rivet, and the like. A material bond is material bonding such as welding, diffusion welding, thermo-compression bonding, soldering, and the like.

In an implementation of an embodiment of an impact motion tracking system according to FIG. 3, the motion tracking sensors 3 of an arm portion 12 of a crash test dummy 1 desirably can include a back of hand sensor 301, a wrist sensor 302, a lower arm sensor 303, an elbow sensor 304, an upper arm sensor 305, a shoulder sensor 305, a shoulder/clavicle sensor 306 and a clavicle sensor 308. In an implementation of an embodiment of an impact motion tracking system according to FIG. 4, the motion tracking sensors 3 of a body portion 13 of a crash test dummy 1 desirably can include a head sensor 309, an upper neck sensor 310, a lower neck sensor 311, an upper spine sensor 312, an upper rip cage sensor 313, a lower rip cage sensor 314, a lower spine sensor 315, a pelvis sensor 316, an acetabulum sensor 317, a femur sensor 318, a knee sensor 319, a lower leg sensor 320, an ankle sensor 321, a foot sensor 322 and a toe sensor 323.

In an implementation of an embodiment of an impact motion tracking system according to FIG. 5, the motion tracking sensors 3 of a vehicle to be crashed 2 desirably can include a left front bumper sensor 331, a right front bumper sensor 331', an engine top sensor 332, a steering wheel sensor 333, a driver seat sensor 334, a left door sensor 335, a right door sensor 335', a back seat sensor 336, a left B pillar sensor 337, a right B pillar sensor 337' and a trunk sensor 338.

Yet other an implementations of an embodiment of an impact motion tracking system according to the present invention may include positioning a motion tracking sensor at other object portions of the at least one a crash test dummy and a vehicle to be crashed, and some examples of such substitute placements or replacements include a bottom engine sensor, a bottom seat sensor, a floor pan sensor, and the like.

In accordance with the impact motion tracking system, during a crash test, the reference magnetic measurement module 32' will not change its position, and also the strength of the magnetic field distortion at the reference magnetic measurement 32' module will not change. The reference magnetic measurement module 32' of the crash test dummy 1 establishes a center of a three-dimensional coordinate system for tracking the impact motion of the crash test dummy 1. In an implementation of an embodiment of an impact motion tracking system, a magnetic measurement module 32' of the pelvis sensor 316 desirably serves as a reference for other magnetic measurement modules 32 of the back of hand sensor 301, the wrist sensor 302, and the like. The reference magnetic measurement module 32' of the vehicle to be crashed 2 establishes a center of a three-dimensional coordinate system for tracking the impact motion of the vehicle to be crashed 2. In an implementation of an embodiment of an impact motion tracking system, a magnetic measurement module 32' of the trunk sensor 338 serves as a reference for other magnetic measurement modules 32 of the left front bumper sensor 331, the right front bumper sensor 331', and the like.

At least one signal acquisition device 41 is provided for receiving measured signals from the motion tracking sensor 3. A signal acquisition device 41 may be provided in a thorax 15 of the crash test dummy 1 or in the trunk 28 of the vehicle to be crashed 2. The signal acquisition device 41 comprises a control circuit, a storage device and an interface. The signal acquisition device 41 may be electrically connected to the magnetic measurement modules 32, 32' and to the inertial measurement modules 33 by means of electric signal conductors (not shown in the figures). The measured signals are transmitted by means of said electric conductors from the magnetic measurement modules 32, 32' and from the inertial measurement modules 33 to the signal acquisition device 41. The control circuit is configured to amplify and digitize the received measured signals in real time. Real time in the sense of the present invention means data amplification and data digitalization within one msec. The storage device is configured to digitize and store the measured signals. The interface may be wireless or wired. The signal acquisition device 41 can be controlled by means of the interface. Independent operation of the signal acquisition device 41 is ensured by an energy storage (not shown in the figures).

The signal acquisition device 41 is configured with sufficient channels to receive and store measured signals from a large number of magnetic measurement modules 32, 32' and inertial measurement modules 33. Preferably, the signal acquisition device 41 has at least 192 channels for at least 32 magnetic measurement modules 32, 32' and for at least 32 inertial measurement modules 33. Each magnetic measurement modules 32, 32' and inertial measurement modules 33 is configured to measure in three dimensions with a time resolution of less than 0.02 msec. Preferably, the signal acquisition device 41 has a sampling rate of at least 9.6 MS/s. Preferably, the impact motion tracking system is configured to track the at least one of a crash test dummy 1 and a vehicle to be crashed 2 with a spatial resolution of less than 2 mm in each of the three dimensions and a time resolution of less than 0.02 msec.

In accordance with the impact motion tracking system, an electronic processor 4 can be provided so that stored measured signals can be transferred to the electronic processor 4 after the crash test for offline motion analysis. As schematically shown in FIGS. 4 and 5, the impact motion tracking system can include a signal transmission 42 that is configured for transferring stored measured signals to the electronic processor 4. The electronic processor 4 desirably comprises a control circuit, a storage device and an interface. The interface may be wireless or wired. The signal transmission 42 is configured to use the interface of the signal acquisition device 41 and of the electronic processor 4. Thus, the electronic processor 4 receives transmitted measured signals from the magnetic measurement modules 32, 32' and the inertial measurement modules 33.

The control circuit of the electronic processor 4 is configured to execute at least one software program product. This software product is configured to derive impact motion information for an object portion 10, 20 of at least one of the crash test dummy 1 and the vehicle to be crashed 2 based on said transmitted measured signals. Said impact motion information can be described as a three-dimensional point vector. The impact motion information may be a position in a three-dimensional space of said object portion 10, 20 or an orientation in a three-dimensional space of said object portion 10, 20. The impact motion information desirably is obtained by the software program product from a double integration in time of transmitted measured signals from the inertial measurement modules 33. Transmitted measured signals from the magnetic measurement modules 32, 32' provide magnetic motion information. Also the magnetic motion information can be described by the software program product as a three-dimensional point vector.

In accordance with the present invention, magnetic motion information desirably is corrected. The gravitation acceleration in Earth coordinates is known and always down, and local magnetic fields can be measured by each magnetic measurement module 32, 32' for an inactive transmitter module 30. Preferably, this measurement of the gravitation acceleration and of local magnetic fields is done before and after the crash test. Thus, the software program product subtracts the gravitation acceleration and local magnetic fields from the magnetic motion information. Said subtraction results in a corrected magnetic motion information, where the undesirable effect of gravitation acceleration and of local magnetic fields is reduced. Preferably, said corrected magnetic motion information is used in lieu of magnetic motion information.

Impact motion information is calibrated with magnetic motion information. The software program product is configured to compare impact motion information with magnetic motion information and derive calibrated motion information. Said calibration reduces undesirable offset errors and misalignment errors of the inertial measurement modules 33.

Magnetic motion information itself is calibrated. The software program product is configured to treat magnetic motion information from a magnetic measurement module 32' of the pelvis sensor 316 as referential magnetic motion information for magnetic motion information from other magnetic measurement modules 32 of the back of hand sensor 301, the wrist sensor 302, and the like. And the software program product is configured to treat magnetic motion information from a magnetic measurement module 32' of the trunk sensor 338 as referential magnetic motion information for magnetic motion information from other magnetic measurement modules 32 of the left front bumper sensor 331, the right front bumper sensor 331', and the like. In accordance with the impact motion tracking system, during a crash test, the reference magnetic measurement module 32' will not change its position, and also the strength of the magnetic field distortion at the reference magnetic measurement 32' module will not change. Thus, the software program product is configured to calibrate magnetic motion information from other magnetic measurement modules 32 with referential magnetic motion information from the reference magnetic measurement module 32'.

Calibrated impact motion information of an object portion 10, 20 after a crash test provides detailed deformation information of the object portion 10, 20. Before the crash test, calibrated impact motion information of the object portion 10, 20 is described as an initial three-dimensional point vector of the object portion 10, 20. After the crash test, calibrated impact motion information of the object portion 10, 20 is described as a final three-dimensional point vector of the object portion 10, 20. Preferably, for the crash test dummy 1, the pelvis 16 serves as the reference object portion, and a three-dimensional point vector of the pelvis 16 serves as the reference three-dimensional point vector before, during and after the crash test. Preferably, for the vehicle to be crashed 2, the trunk 28 serves as the reference object portion, and a three-dimensional point vector of the trunk 28 serves as the reference three-dimensional point vector before, during and after the crash test. For the crash test dummy 1, a difference between the final three-dimensional point vector of an object portion 10 other than the pelvis 16 and the reference three-dimensional point vector relate to deformation information of the object portion 10. For the vehicle to be crashed 2, a difference between the final three-dimensional point vector of an object portion 20 other than the trunk 28 and the reference three-dimensional point vector relate to deformation information of the object portion 20.

Figure 6:
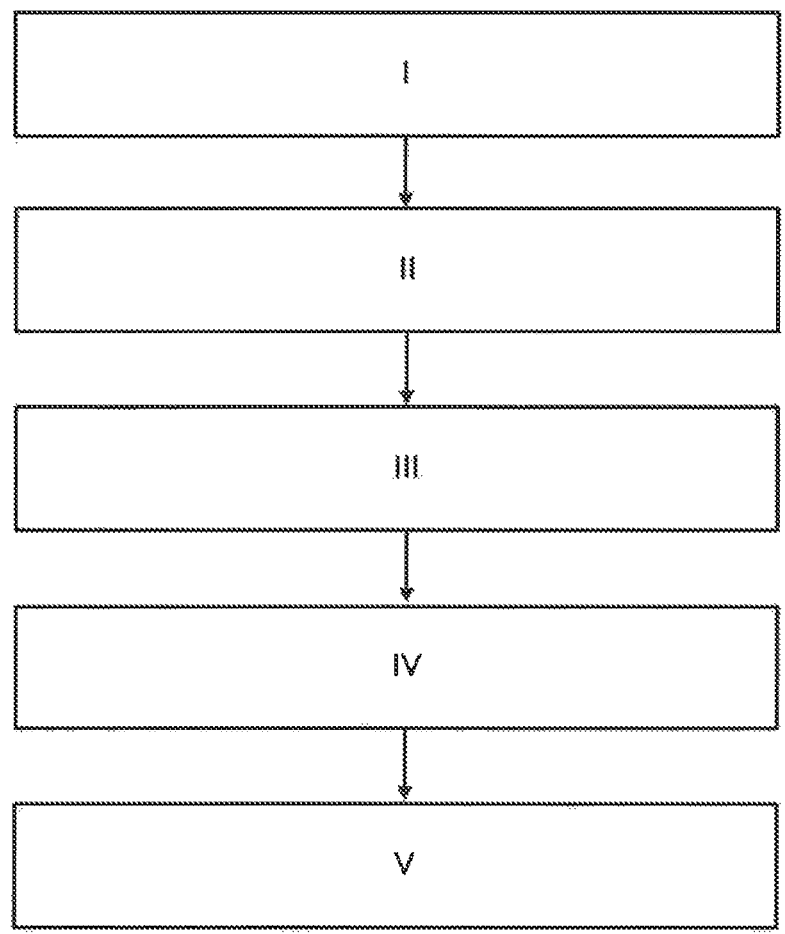
FIG. 6 shows method steps for tracking an object with the impact motion tracking system of FIG. 1 before, during and after a crash test.

FIG. 6 schematically shows method steps of the tracking of at least one of a crash test dummy 1 and a vehicle to be crashed 2 with the impact motion tracking system of FIG. 1 before, during and after a crash test. In a first method step I, magnetic fields are generated by a transmitter module 30. In a second method step II, several magnetic measurement modules 32, 32' measure the generated magnetic fields and several inertial measurement modules 33 measure at least one of a linear acceleration and an angular acceleration. In a third method step III, an electronic processor 4 receives measured signals from said magnetic measurement modules 32, 32' and said inertial measurement modules 33. In a forth method step IV, said electronic processor 4 derives an impact motion information based on received measured signals from the inertial measurement modules 33 and said electronic processor 4 derives a magnetic motion information based on received measured signals from the magnetic measurement modules 32, 32'. In a fifth method step V, said electronic processor 4 calibrates magnetic motion information from other magnetic measurement modules 32 with referential magnetic motion information from a reference magnetic measurement module 32'. The calibration results in calibrated motion information of an object portion 10, 20. The calibration of magnetic motion information from other magnetic measurement modules 32 with referential magnetic motion information from a reference magnetic measurement module 32' occurs periodically in time intervals of less than 0.02 msec. That means, each magnetic motion information measured with a time resolution of less than 0.02 msec from a magnetic measurement module 32 is calibrated with a reference magnetic motion information measured with a time resolution of less than 0.02 msec from a reference magnetic measurement module 32'.

LIST OF REFERENCE NUMERALS 1 crash test dummy
2 vehicle to be crashed 3 motion tracking sensor
4 electronic processor
5 barrier mass
10 object portion
11 skeleton
12 arm portion
13 body portion
15 thorax
16 pelvis
20 object portion
21 front bumper
22 engine
23 steering wheel
24 door
26 seat
27 B pillar
28 Trunk
30 transmitter module
31 housing
32, 32' magnetic measurement module
33 inertial measurement module
34 fixed connection
41 signal acquisition device
42 signal transmission
301 back of hand sensor
302 wrist sensor
303 lower arm sensor
304 elbow sensor
305 upper arm sensor
306 shoulder sensor
307 shoulder/clavicle sensor
308 clavicle sensor
309 head sensor
310 upper neck sensor
311 lower neck sensor
312 upper spine sensor
313 upper rip cage sensor
314 lower rip cage sensor
315 lower spine sensor
316 pelvis sensor
317 acetabulum sensor
318 femur sensor
319 knee sensor
320 lower leg sensor
321 ankle sensor
322 foot sensor
323 toe sensor
331, 331' front bumper
332 engine top sensor
333 steering wheel sensor
334 driver seat sensor
335, 335' door sensor
336 back seat sensor
337, 337' B pillar sensor
338 trunk sensor
I generation of magnetic fields
II measurement of magnetic fields and of acceleration
III reception of measured signals
IV derivation of impact motion information and of magnetic motion information
V calibration of magnetic motion information

What is claimed is:

1. An impact motion tracking system for tracking in a three-dimensional space in a crash an object having at least one object portion, wherein the object is a crash test dummy or a vehicle to be crashed, the impact motion tracking system comprising:

a transmitter module configured to generate magnetic fields and carried at a fixed location of the object;
a motion tracking sensor, which includes a housing, an inertial measurement module disposed in the housing, and a first magnetic measurement module disposed in the housing at a first disposition with respect to the inertial measurement module prior to the crash, wherein the first magnetic measurement module having a fixed positional relationship with the at least one object portion of the object, wherein the first magnetic measurement module is configured and disposed to measure the magnetic fields generated by the transmitter module;
an electronic processor configured to receive measured signals from the motion tracking sensor;
wherein the inertial measurement module is configured and disposed to measure at least one of a linear acceleration and an angular acceleration;
wherein the electronic processor is configured to derive an impact motion information for the at least one object portion of the object based on received measured signals from the inertial measurement module;
wherein the electronic processor is configured to derive a magnetic motion information for the at least one object portion of the object based on received measured signals from the first magnetic measurement module; and
wherein the electronic processor is configured to periodically calibrate impact motion information with magnetic motion information to compensate for any error attributable to any change in the first disposition.

2. An impact motion tracking system according to claim 1, further comprising:
a second magnetic measurement module having a fixed positional relationship with the first magnetic measurement module;
wherein the electronic processor is configured to regard the first magnetic measurement module to serve as a reference magnetic measurement module for the at least one object portion of the object; and
wherein the electronic processor is configured to periodically calibrate magnetic motion information from the second magnetic measurement module with referential magnetic motion information from the first magnetic measurement module.

3. An impact motion tracking system according to claim 2, further comprising a crash test dummy having a pelvis, wherein the second magnetic measurement module is positioned at the pelvis.

4. An impact motion tracking system according to claim 2, further comprising a vehicle to be crashed having a trunk, wherein the first magnetic measurement module is positioned at the trunk.

5. An impact motion tracking system according to claim 1, wherein the first magnetic measurement module is configured to measure a gravitation acceleration and a local magnetic field; and wherein the electronic processor is configured to subtract the measured gravitation acceleration and the measured local magnetic field from the magnetic motion information and provide a corrected magnetic motion information in lieu of the magnetic motion information.

6. An impact motion tracking system according to claim 1, wherein the object is a crash test dummy, wherein for said crash test dummy, the motion tracking sensor is fixed to a pelvis of the crash test dummy and the first magnetic measurement module is configured to serve as a reference magnetic measurement module; and wherein the electronic processor is configured so that after a crash test, a difference in calibrated impact motion information of an object portion other then said pelvis with said pelvis provides deformation information of said object portion other then said pelvis.

7. An impact motion tracking system according to claim 1, wherein the object is a vehicle, wherein for the vehicle to be crashed, the motion tracking sensor is fixed to a trunk of the vehicle and the first magnetic measurement module is configured to serve as a reference object portion; and wherein the electronic processor is configured so that after a crash test, a difference in calibrated impact motion information of an object portion other then said trunk with said trunk provides deformation information of said object portion other then said trunk.

8. An impact motion tracking system according to claim 1, wherein said motion tracking sensor is configured to withstand an impact motion induced by a linear acceleration of up to 60 g for a period of at least 3 msec or by an angular acceleration of up to 1500°/sec.

9. An impact motion tracking system according to claim 1, further comprising a signal acquisition device disposed in at least one of a thorax of said crash test dummy and a trunk of said vehicle to be crashed; wherein said signal acquisition device is configured to receive measured signals from said motion tracking sensor; and wherein said signal acquisition device is configured to amplify and digitize received measured signals in real time.

10. An impact motion tracking system according to claim 1, further comprising a signal acquisition device electrically connected to the motion tracking sensor and having a sampling rate of at least 9.6 MS/s; and wherein the signal acquisition device and the motion tracking sensor are configured to provide the impact motion tracking system with a spatial resolution of less than 2 mm in each of the three dimensions and a time resolution of less than 0.02 msec.

11. An impact motion tracking system according to claim 1, wherein said motion tracking sensor has a fixed connection with an object portion; wherein during and after the impact motion, a mutual distance between the motion tracking sensor and the object portion to which object portion the motion tracking sensor has a fixed positional relationship changes less than 1 mm.

12. An impact motion tracking system according to claim 11, wherein said fixed connection is directly made between said housing of said motion tracking sensor and a skeleton of said crash test dummy.

13. An impact motion tracking system according to claim 11, wherein said fixed connection is directly made between said housing of said motion tracking sensor and an object portion of said vehicle to be crashed.

14. An impact motion tracking system according to claim 1, wherein at least one of said transmitter module, said first magnetic measurement module and said inertial measurement module is embedded inside said object portion.

15. A method of tracking impact motion of an object in a three-dimensional space, the method comprising:
generating magnetic fields with a transmitter module;
measuring said generated magnetic fields at at least a first place, said first place having a fixed positional relationship with an object portion of said object;
measuring at least one of a linear acceleration and an angular acceleration at said first place, said first place having a first disposition with respect to said at least one object portion;
receiving signals for said measured generated magnetic fields and for said at least one of the measured linear acceleration and the measured angular acceleration;
deriving an impact motion information for said object portion based on received signals for said at least one of the measured linear acceleration and the measured angular acceleration;
deriving a magnetic motion information for said object portion based on received signals for said measured generated magnetic fields;
periodically calibrating impact motion information with the magnetic motion information to compensate for any error attributable to any change in the first disposition; and
said object being at least one of a crash test dummy and a vehicle to be crashed.

16. The method according to claim 15, further comprising the step of treating magnetic motion information measured at a pelvis of said crash test dummy as a referential magnetic motion information; and periodically calibrating magnetic motion information from other object portions of said crash test dummy with said reference magnetic motion information.

17. The method according to claim 15, further comprising the step of treating magnetic motion information measured at a trunk of said vehicle to be crashed as a referential magnetic motion information; and periodically calibrating magnetic motion information from other object portions of said vehicle to be crashed with said reference magnetic motion information.

* * * * *